(12) United States Patent
Yeshurun et al.

(10) Patent No.: US 7,588,552 B2
(45) Date of Patent: Sep. 15, 2009

(54) DEVICES AND METHODS FOR TRANSPORTING FLUID ACROSS A BIOLOGICAL BARRIER

(75) Inventors: Yehoshua Yeshurun, Haifa (IL); Meir Hefetz, Mizpeh Harashim (IL); Gil Fruchtman, Kiryat Tivon (IL); Yotam Levin, Nes Ziona (IL)

(73) Assignee: Nano Pass Technologies Ltd., Haifa (IL)

(*) Notice: Subject to any disclaimer, the term of this patent is extended or adjusted under 35 U.S.C. 154(b) by 613 days.

(21) Appl. No.: 10/506,904

(22) PCT Filed: Mar. 4, 2003

(86) PCT No.: PCT/IL03/00165

§ 371 (c)(1),
(2), (4) Date: Sep. 7, 2004

(87) PCT Pub. No.: WO03/074102

PCT Pub. Date: Sep. 12, 2003

(65) Prior Publication Data

US 2005/0165358 A1    Jul. 28, 2005

(30) Foreign Application Priority Data

Mar. 4, 2002 (IL) ...................................... 148486
Mar. 7, 2002 (IL) ...................................... 148567
Jul. 14, 2002 (IL) ...................................... 150729

(51) Int. Cl.
A61B 17/20    (2006.01)

(52) U.S. Cl. .......................................... 604/22; 604/46

(58) Field of Classification Search .................... 604/19, 604/22, 48, 500, 501, 506, 511, 46, 47, 93.01
See application file for complete search history.

(56) References Cited

U.S. PATENT DOCUMENTS 2,704,542 A    3/1955    Scherer
3,908,651 A    9/1975    Fudge (Continued)

FOREIGN PATENT DOCUMENTS

WO    WO99/64580    6/1999

(Continued)

OTHER PUBLICATIONS

Micro machined needles for the transdermal deliver of drugs S.H.S. Henry et al pp. 494-498 (Mems 98, Heidleberg, Germany Jan. 1998).

(Continued)

*Primary Examiner*—Nicholas D Lucchesi
*Assistant Examiner*—Christopher D Koharski
(74) *Attorney, Agent, or Firm*—Mark M. Friedman

(57) ABSTRACT

A device (10) and method for transporting fluids across biological barriers enhances penetration of a biological barrier by the use of directional insertion, preferably with asymmetric microneedles (18) and/or microneedles (18) with sharp edges. Additionally, or alternatively, adhesion followed by alteration of contact geometry is employed to stretch the biological barrier across the microneedles (18), thereby also enhancing penetration. Also disclosed is a device (10) and method which combine shallow penetration by hollow microneedles (18) with jet injection via the microneedles (18) to achieve a total liquid penetration depth greater than the mechanical penetration depth of the microneedles (18).

27 Claims, 10 Drawing Sheets

U.S. PATENT DOCUMENTS

| | | | |
|---|---|---|---|
| 3,964,482 A * | 6/1976 | Gerstel et al. | 604/890.1 |
| 4,031,783 A * | 6/1977 | Paul et al. | 81/9.22 |
| 4,695,273 A * | 9/1987 | Brown | 604/173 |
| 4,832,683 A | 5/1989 | Idemoto et al. | |
| 5,399,163 A * | 3/1995 | Peterson et al. | 604/68 |
| 5,445,611 A * | 8/1995 | Eppstein et al. | 604/501 |
| 5,499,972 A | 3/1996 | Parsons | |
| 6,063,053 A | 5/2000 | Castellano et al. | |
| 6,102,896 A * | 8/2000 | Roser | 604/218 |
| 6,224,567 B1 | 5/2001 | Roser | |
| 6,264,629 B1 | 7/2001 | Landau | |
| 6,319,224 B1 * | 11/2001 | Stout et al. | 604/68 |
| 6,319,230 B1 * | 11/2001 | Palasis et al. | 604/164.01 |
| 6,440,096 B1 * | 8/2002 | Lastovich et al. | 604/27 |
| 6,533,949 B1 * | 3/2003 | Yeshurun et al. | 216/11 |
| 6,537,242 B1 * | 3/2003 | Palmer | 604/22 |
| 6,589,202 B1 * | 7/2003 | Powell | 604/27 |
| 6,607,513 B1 * | 8/2003 | Down et al. | 604/239 |
| 6,611,707 B1 * | 8/2003 | Prausnitz et al. | 604/21 |
| 6,689,100 B2 * | 2/2004 | Connelly et al. | 604/117 |
| 6,749,792 B2 * | 6/2004 | Olson | 264/328.1 |
| 6,780,171 B2 * | 8/2004 | Gabel et al. | 604/181 |
| 6,924,087 B2 * | 8/2005 | Yeshurun et al. | 430/313 |
| 2002/0032415 A1 * | 3/2002 | Trautman et al. | 604/272 |
| 2002/0038101 A1 * | 3/2002 | Avrahami et al. | 604/20 |
| 2002/0042589 A1 * | 4/2002 | Marsoner | 604/46 |
| 2003/0009113 A1 * | 1/2003 | Olson | 600/573 |
| 2005/0065463 A1 * | 3/2005 | Tobinaga et al. | 604/46 |
| 2005/0165358 A1 * | 7/2005 | Yeshurun et al. | 604/173 |
| 2005/0245877 A1 * | 11/2005 | Wilkinson et al. | 604/173 |
| 2005/0261631 A1 * | 11/2005 | Clarke et al. | 604/173 |

FOREIGN PATENT DOCUMENTS

| | | |
|---|---|---|
| WO | WO00/74763 | 12/2000 |
| WO | WO02/17985 | 8/2001 |
| WO | WO01/66065 | 9/2001 |

OTHER PUBLICATIONS

Three dimensional hollow micro needle and microtube arrays DV McAllister et al (Transducer 99, Sendai Japan Jun. 1999).

An array of hollow micro-capillaries for the controlled injection of genetic materials into animal/plant cells' K Chun et al pp. 406-411 (Mems 99, Orlando, Florida Jan. 1999).

Injection of DNA into plant and animal tissues with micromechanical piercing structures W Trimmer et al (IEEE workshop on MEMS, Amsterdam Jan. 1995) pp. 111-115.

* cited by examiner

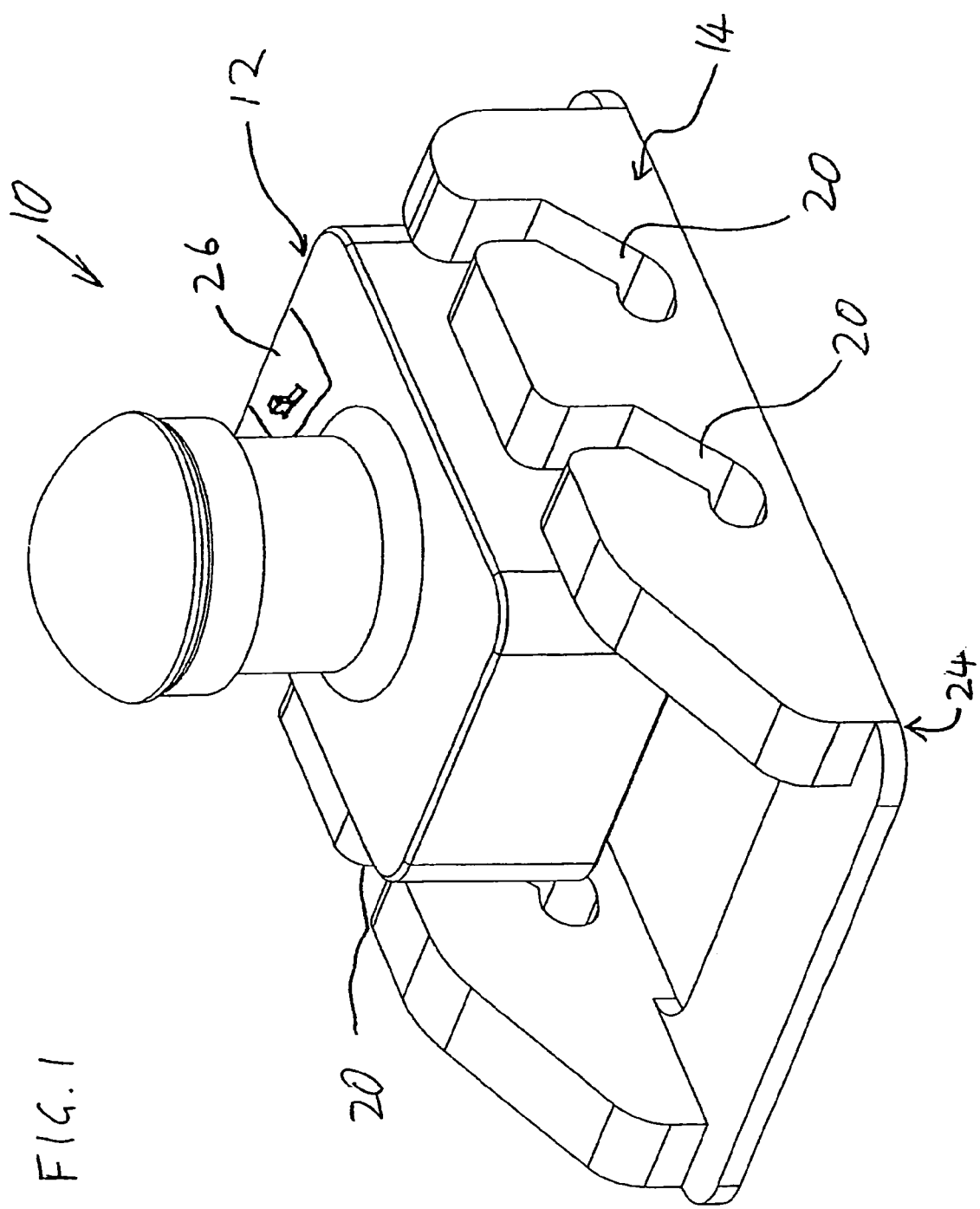

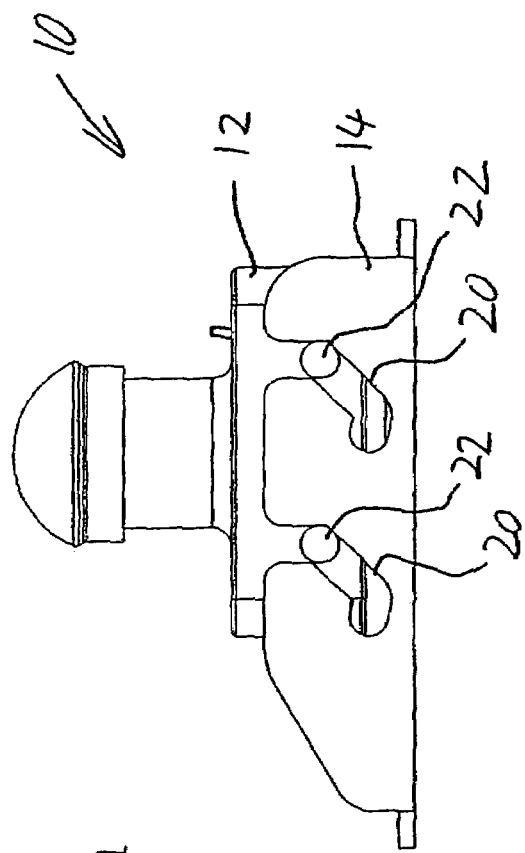
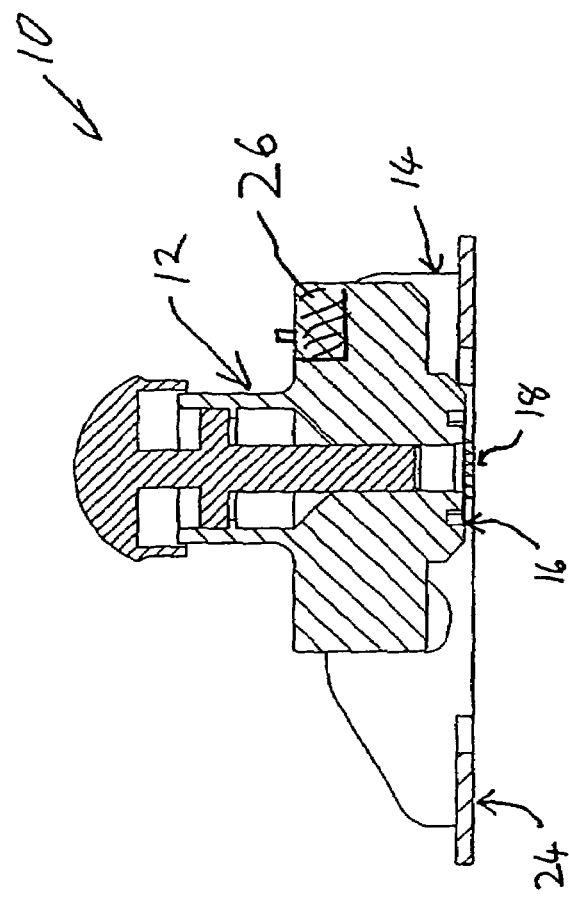
FIG. 2A
FIG. 2B

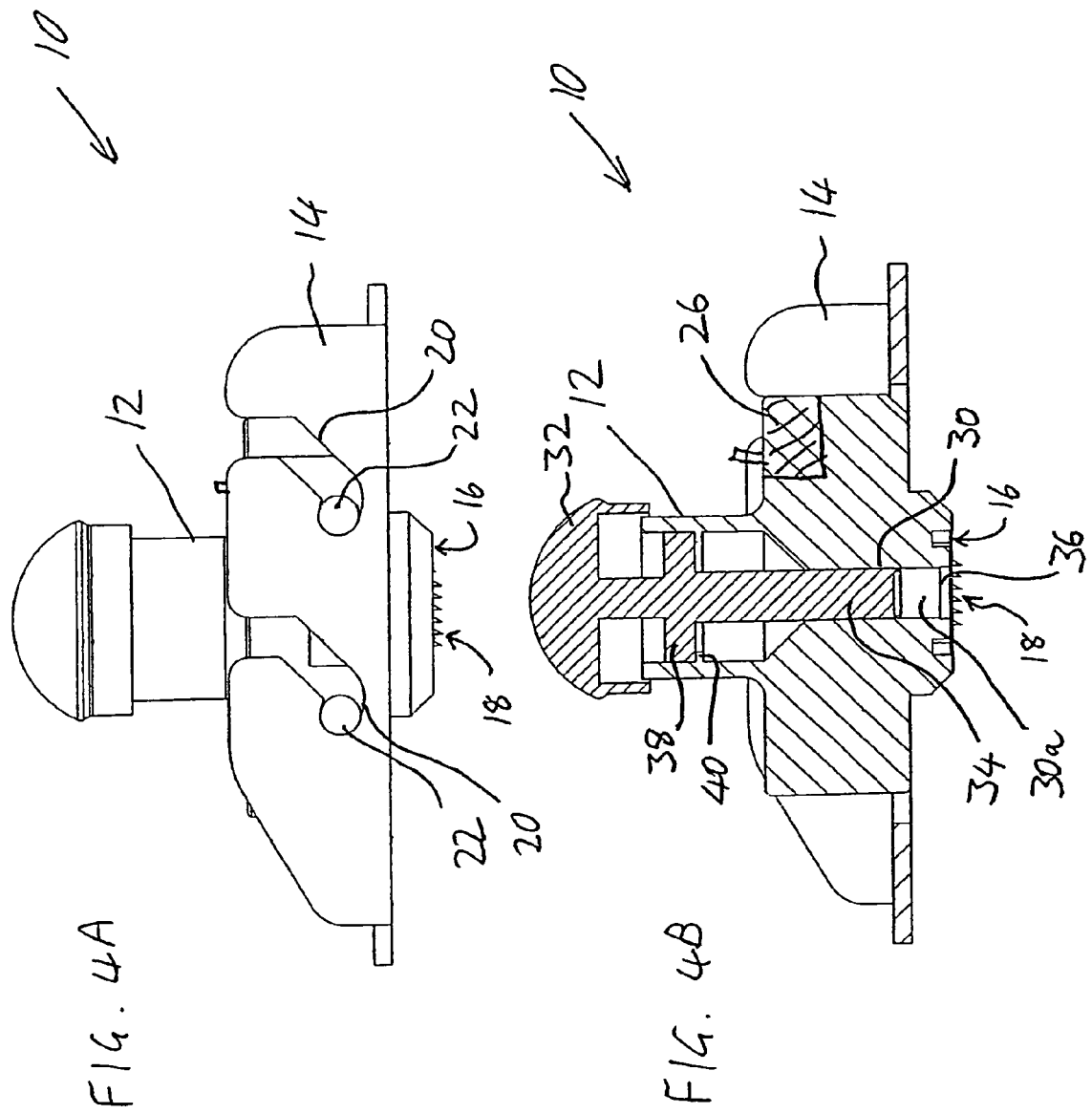

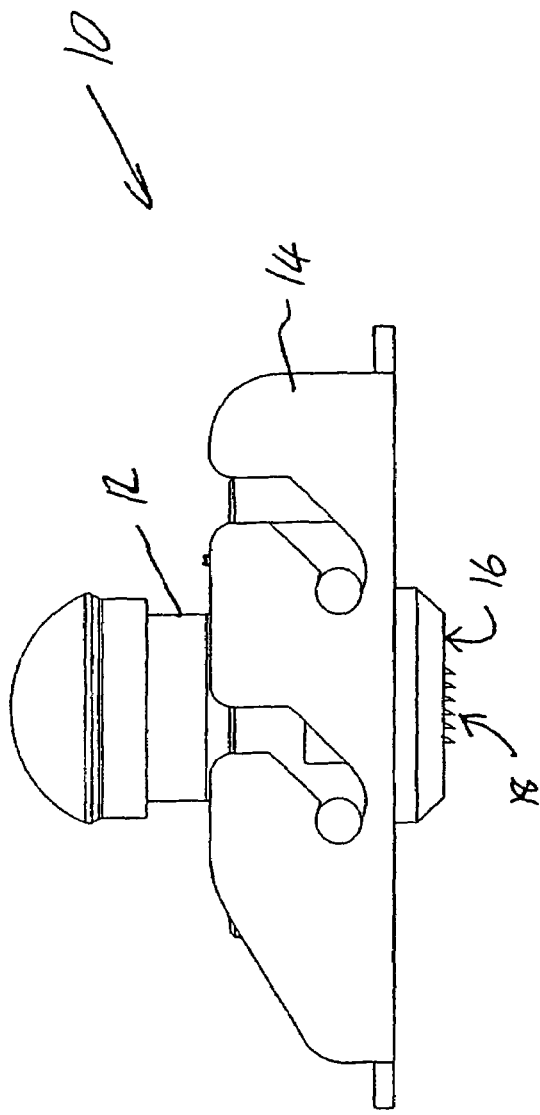
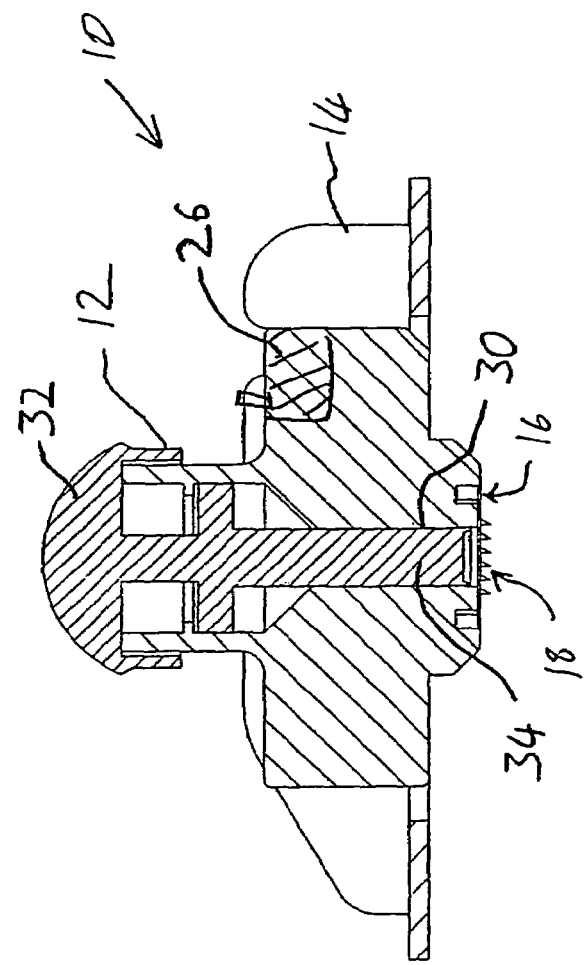
FIG. 5A
FIG. 5B

DEVICES AND METHODS FOR TRANSPORTING FLUID ACROSS A BIOLOGICAL BARRIER

FIELD AND BACKGROUND OF THE INVENTION

The present invention relates devices and methods for transporting fluids across biological barriers, for example, for purposes of administering drugs, sampling the tissue for the presence and concentration of substances, or for any other medical or research purpose. More specifically, the present invention relates to microneedle devices with features and corresponding methods for enhancing skin penetration, as well as to devices and methods which employ a combination of shallow penetration by hollow microneedles followed by jet injection via the microneedles.

Research and development of microneedle arrays has advanced in recent years as part of a system for drug delivery or biological sampling. In these applications, the microneedle approach shows clear advantages over competing methods of transferring fluids through skin or other barriers. In contrast to hypodermic needles, microneedles are relatively painless and can be self administered or administered by nonprofessionals. In addition, they overcome the molecular size limitations characteristic of conventional transdermal patches. Examples of such work may be found in PCT Publications Nos. WO 01/66065 and WO 02/17985, both co-assigned with the present application. These publications are hereby incorporated by reference as if set out in their entirety herein. Other relevant publications include WO 99/64580 and WO 00/74763 to Georgia Tech Research Corp., as well as in the following scientific publications: "Micro machined needles for the transdermal delivery of drugs", S. H. S. Henry et al. (MEMS 98, Heildelberg, Germany, January 1998); "Three dimensional hollow micro needle and microtube arrays", D. V. McAllister et al. (Transducer 99, Sendai, Japan, June 1999); "An array of hollow micro-capillaries for the controlled injection of genetic materials into animal/plant cells", K. Chun et al. (MEMS 99, Orlando, Fla., January 1999); and "Injection of DNA into plant and animal tissues with micromechanical piercing structures", W. Trimmer et al. (IEEE workshop on MEMS, Amsterdam, January 1995). The aforementioned PCT applications disclose the use of hollow microneedles to provide a flow path for fluid flow through the skin barrier.

While hollow microneedles are potentially an effective structure for transferring fluids across a biological barrier, the devices proposed to date suffer from a number of drawbacks that limit or prevent their functionality. Current microneedle array devices do not reliably penetrate the biological barrier, preventing or diminishing cross-barrier transfer of fluids. In the case of administering drugs through human skin, the transfer is ineffective if the microneedle does not pierce at least the stratum corneum layer. In many cases, the skin surface is elastic enough to stretch around each microneedle without being pierced.

Various approaches have been proposed to ensure sufficient penetration into the skin. One approach has been to use very long and sharp microneedles. While achieving greater penetration, the microneedles produced by this method are more fragile and more difficult to manufacture. A different approach is suggested by the aforementioned WO 00/74763 to Georgia Tech which proposes various complicated mechanical devices to stretch the skin. U.S. Pat. No. 6,440,096 to Lastovish et al. discloses an arrangement for stretching the skin by use of a suction cup constructed around the device.

Yet another approach is based on diminishing the elasticity of the skin by freezing or otherwise changing the mechanical properties of the skin prior to penetration. All of these approaches clearly suffer from complexity of use and/or production.

In the field of surgical tools for use during surgical procedures, it is known to use ultrasonic vibrations to enhance the effect of a cutting or separating tool as in U.S. Pat. No. 4,832,683 to Idemoto et al. Ultrasonic vibrations have been a feature of surgical devices intended for use by skilled personnel, but have not been previously applied to enhance penetration of microneedles into a biological barrier.

It is also known to employ a needleless injector as an alternative to a hollow needle for injection of fluid into the body. These injectors use a fine stream or "jet" of pressurized liquid to penetrate the skin. Early designs used high pressure throughout the injection, to punch a hole through the tough stratum corneum and epidermis. However, the bulk of the injection could then be infused along the initial track under much lower pressure. U.S. Pat. No. 2,704,542 to Scherer and U.S. Pat. No. 3,908,651 to Fudge disclose examples of this design. Ultimately, the engineering demands of changing the pressure during the injection and resulting complexity, the cost, and the pain associated, have limited the use of such devices.

In most cases, modern high-pressure needleless jet injectors are driven by pressure from a pressurized gas cylinder as exemplified by U.S. Pat. Nos. 6,063,053 and 6,264,629. 5,499,972 teaches a jet injection device powered by a powerful cocked spring. Of most relevance to the present invention are U.S. Pat. Nos. 6,102,896 and 6,224,567 which teach a jet injection device where the pressure is generated manually by pressing on a cap. When sufficient force is applied, a mechanical obstruction is overcome to actuate the pressure jet.

While jet injectors offer advantages of somewhat reduced pain and potentially improved hygiene compared to conventional needle injections, they still suffer from many drawbacks. Most notably, since there is no sealed conduit between the drug supply and the target tissue, significant wastage of the drug occurs. This also results in lack of precision in the administered dosage of a drug. Furthermore, penetration through the strong tissue of the upper layers of the skin requires high activation pressures which typically require complex and expensive systems. The use of purely manual pressure for activation may raise questions of reliability.

There is therefore a need for devices and methods which would enhance the penetration of a biological barrier, particularly the stratum corneum, by microneedles. There is also a need for a device and method which would achieve relatively painless shallow penetration by use of hollow microneedles followed by jet injection via the microneedles. Since 70% of the resistance of the skin is attributed to the stratum corneum layer, mechanical penetration of this layer prior to use of jet injection allows use of lower energy jet injection streams and correspondingly simpler actuation mechanisms.

SUMMARY OF THE INVENTION

The present invention is a device and method for transporting fluids across biological barriers.

According to the teachings of the present invention there is provided, a microneedle device for transporting fluid across a biological barrier, the device comprising: (a) a fluid transport configuration including: (i) a substrate defining a substantially planar surface, (ii) a plurality of microneedles projecting from the surface; (b) an abutment member having at least one abutment surface for abutting the biological barrier; and (c) a displacement mechanism mechanically linking between the abutment member and the fluid transport configuration, the displacement mechanism defining a path of movement of the fluid transport configuration relative to the abutment surface, at least part of the path of movement having a non-zero component parallel to the surface.

According to a further feature of the present invention, each of the microneedles has a base-to-tip vector defined as a vector from a centroid of a base area of the microneedle to a centroid of a penetrating tip of the microneedle, the microneedles being asymmetrical such that the base-to-tip vector is non-perpendicular to the surface, a direction parallel to a projection of the base-to-tip vector on to the planar surface being taken to define a penetration direction, and wherein at least part of the path of movement has a non-zero component along the penetration direction.

According to a further feature of the present invention, each of the microneedles is formed with at least two side walls each having a substantially planar face, the side walls being positioned such that an angle between the faces as measured in a plane parallel to the planar surface of the base is no greater than 90°, and preferably between 30° and 70°.

According to a further feature of the present invention, there is also provided a vibration generator associated with the fluid transport configuration and deployed so as to generate vibration of the fluid transport configuration so as to enhance penetration of the microneedles into the biological barrier.

There is also provided according to the teachings of the present invention, a method for transporting fluid across a biological barrier comprising the steps of: (a) providing a fluid transport configuration including: (i) a substrate defining a substantially planar surface, (ii) a plurality of microneedles projecting from the surface; (b) positioning the fluid transport configuration in contact with the biological barrier; and (c) generating a displacement of the fluid transport configuration relative to the biological barrier, the displacement having a non-zero component parallel to the surface.

There is also provided according to the teachings of the present invention, a microneedle device for transporting fluid across a biological barrier, the device comprising: (a) a fluid transport configuration including: (i) a substrate defining a substantially planar surface, and (ii) a plurality of microneedles projecting from the surface; (b) an abutment member having at least one abutment surface for abutting the biological barrier, at least part of the at least one abutment surface being provided with adhesive for maintaining contact between the abutment surface and the biological barrier; and (c) a displacement mechanism mechanically linking between the abutment member and the fluid transport configuration, the displacement mechanism being configured to define a path of movement of the fluid transport configuration relative to the abutment surface, the path of movement carrying the substantially planar surface from an initial position above the at least one abutment surface to a deployed position projecting below the at least one abutment surface for stretching the biological barrier across the substantially planar surface.

According to a further feature of the present invention, the at least one abutment surface substantially encircles the fluid transport configuration when the planar surface is in the deployed position.

There is also provided according to the teachings of the present invention, a method for transporting fluid across a biological barrier, the method comprising: (a) providing: (i) a fluid transport configuration including: a substrate defining a substantially planar surface, and a plurality of microneedles projecting from the surface, and (ii) an abutment member having at least one abutment surface for abutting the biological barrier; (b) causing the at least one abutment surface to temporarily adhere to a surface of the biological barrier; and (c) displacing the fluid transport configuration relative to the abutment surface along a path of movement which carries the substantially planar surface from an initial position above the at least one abutment surface to a deployed position projecting below the at least one abutment surface so as to stretch the biological barrier across the substantially planar surface.

According to a further feature of the present invention, the at least one abutment surface substantially encircles the fluid transport configuration when the planar surface is in the deployed position.

There is also provided according to the teachings of the present invention, a method for injecting fluid through a biological barrier, the method comprising: (a) employing at least one hollow microneedle to penetrate into the biological barrier to a first depth; and (b) generating a high velocity flow of fluid through a bore of the microneedle so as to form a fluid jet with sufficient pressure to penetrate into the biological barrier to a total depth at least one-and-a-half times the first depth.

According to a further feature of the present invention, energy for the generating a high velocity flow is provided exclusively by force applied manually to a flow actuation mechanism.

According to a further feature of the present invention, the flow actuation mechanism is configured to generate a pressure of between 1000 and 1500 PSI.

According to a further feature of the present invention, the first depth is less than 2 mm. According to an alternative feature of the present invention, the first depth is between 0.02 mm and 0.2 mm. According to a still further alternative feature of the present invention, the first depth is between 0.2 mm and 2 mm.

According to a further feature of the present invention, the fluid jet has a diameter of less than 0.1 mm, and preferably between 30 microns and 70 microns.

There is also provided according to the teachings of the present invention, a microneedle device for injecting fluid through a biological barrier, the device comprising: (a) a substrate defining a substantially planar surface; (b) a plurality of microneedles projecting from the surface, each of the microneedles having a conduit extending through at least part of the microneedle and at least part of the substrate; and (c) a flow actuation mechanism in fluid connection with the conduits and configured for generating a driving pressure of at least 1000 PSI so as to produce a high velocity fluid jet emerging from the conduits for penetrating into the biological barrier beyond a depth of penetration of the microneedles.

According to a further feature of the present invention, the flow actuation mechanism is configured to derive the driving pressure exclusively from force applied manually to the flow actuation mechanism.

BRIEF DESCRIPTION OF THE DRAWINGS

The invention is herein described, by way of example only, with reference to the accompanying drawings, wherein:

FIG. 1 is a schematic isometric view of a microneedle device, constructed and operative according to the teachings of the present invention, for transporting fluids across a biological barrier;

FIGS. 2A and 2B are side and cross-sectional views, respectively, taken through the device of FIG. 1 with a fluid transport unit in an initial raised position;

FIGS. 4A and 4B are side and cross-sectional views, respectively, taken through the device of FIG. 1 with the fluid transport unit in a fully lowered position prior to actuation;

FIGS. 5A and 5B are side and cross-sectional views, respectively, taken through the device of FIG. 1 after actuation of the fluid transport unit;

DESCRIPTION OF THE PREFERRED EMBODIMENTS

Figure 3A:
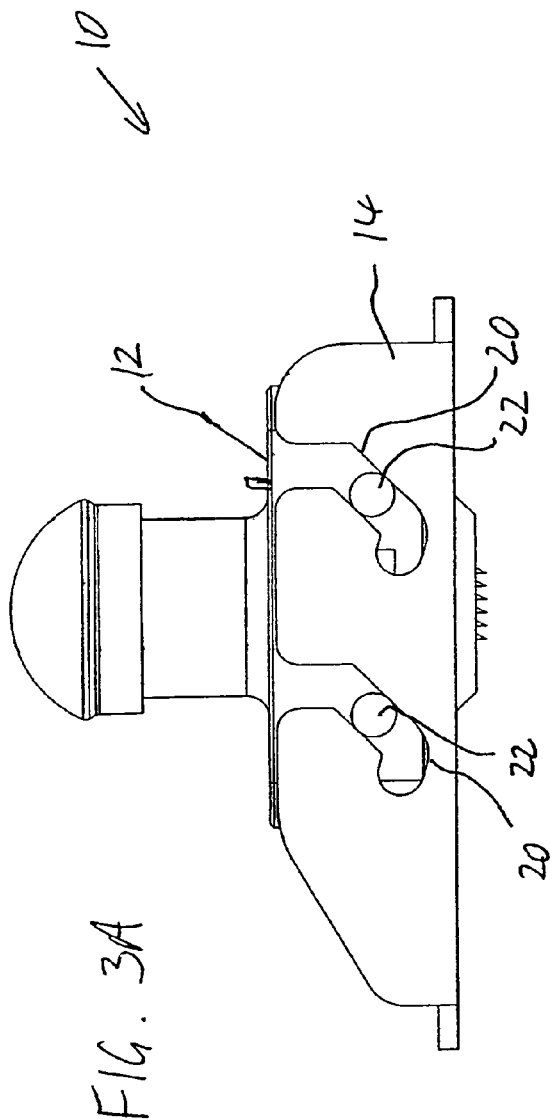
FIGS. 3A and 3B are side and cross-sectional views, respectively, taken through the device of FIG. 1 with the fluid transport unit in a partially lowered position.
Figure 3B:
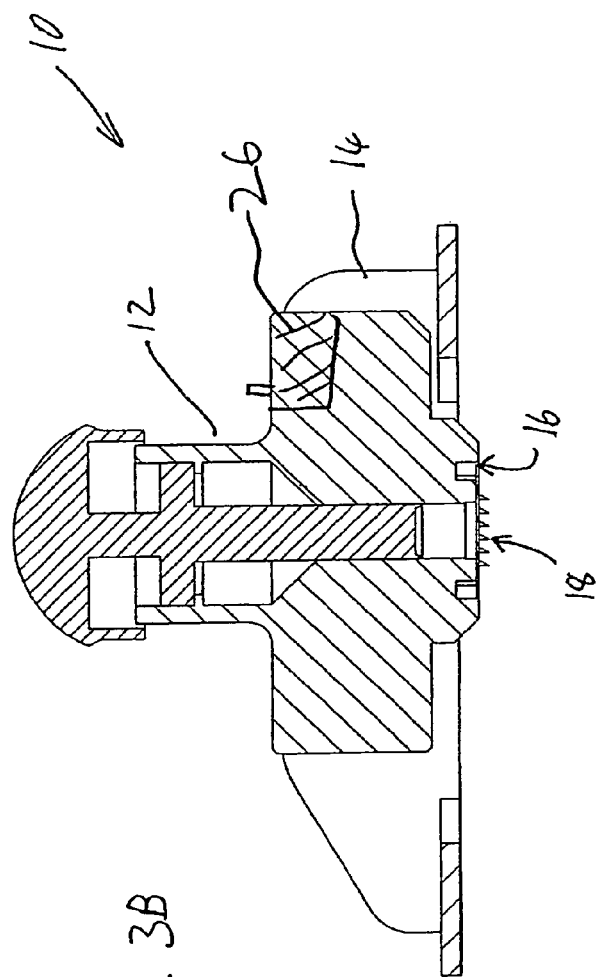

The present invention is a device and method for transporting fluids across biological barriers.

The principles and operation of devices and methods according to the present invention may be better understood with reference to the drawings and the accompanying description.

Before addressing the figures directly, it should be appreciated that the present invention has a number of aspects each of which is believed to be patentable in its own right, but which are most preferably used to advantage when combined in synergy within a single system. Specifically, a first aspect of the invention relates to the use of directional insertion, preferably using asymmetric microneedles, to enhance penetration of the biological barrier. A second aspect relates to the use of adhesion followed by alteration of the geometry so as to stretch the biological barrier across the microneedles, thereby also enhancing penetration. A third aspect relates to the combination of shallow penetration by hollow microneedles followed by jet injection via the microneedles. It will be clear to one ordinarily skilled in the art that each of these aspects of the present invention may be advantageously implemented independent of the other aspects. Nevertheless, by way of non-limiting example, the various aspects will now be described primarily in the context of a particularly preferred implementation which combines all of the aforementioned aspects.

Referring now to the drawings, FIGS. 1 to 5B show a microneedle device, generally designated 10, constructed and operative according to the teachings of the present invention, for transporting fluid across a biological barrier. Generally speaking, device 10 has a fluid transport unit 12 mounted on a base 14. Fluid transport unit 12 is a microneedle-based drug delivery unit having a substrate defining a substantially planar surface 16 with a plurality of microneedles 18 projecting therefrom.

Before addressing the features of this preferred embodiment further, it will be useful to first describe the principles of the penetration enhancement techniques and corresponding structures with reference to FIGS. 6A-6E.

Figure 6A:
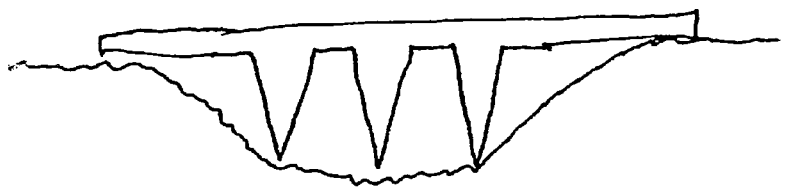
FIG. 6A is a schematic illustration of the problem of elasticity of the skin during perpendicular insertion of microneedles.

Referring firstly to FIG. 6A, this illustrates the problem encountered by conventional attempts at direct perpendicular penetration of the skin by microneedles. Specifically, the flexibility of the skin is particularly pronounced under out-of-plane deformations, allowing the skin to be locally depressed so as to conform to the external shape of the microneedles without allowing proper penetration. This effect seriously impedes, or even prevents, fluid transfer via the microneedles.

Figure 6B:
FIG. 6B is a schematic representation of a directional insertion effect according to the teachings of the present invention.

In contrast, FIG. 6B shows a representation of a directional insertion technique according to the teachings of the present invention which includes generating a displacement of the fluid transport configuration relative to the biological barrier, the displacement having a non-zero component parallel to the surface. In contrast to the out-of-plane flexibility illustrated in FIG. 6A, the in-plane stretching capabilities of the skin are much more limited. These contrasting properties are familiar to us from everyday experience in which relatively blunt objects which do not pierce the skin on localized pressure readily cause scratches under sliding contact conditions. As a result of these properties, a penetration vector which includes a component parallel to the skin surface tends to be much more effective than direct pressure perpendicular to the skin. It is also possible to anchor the skin against in-plane movement around the microneedle insertion region, as will be clear from the following description, thereby further enhancing the sliding penetration effect. Most preferably, this effect is enhanced by providing asymmetric penetrating features and/or a lateral cutting edge for the microneedles, as will be exemplified with reference to FIGS. 7A-11B below.

Figure 6C:
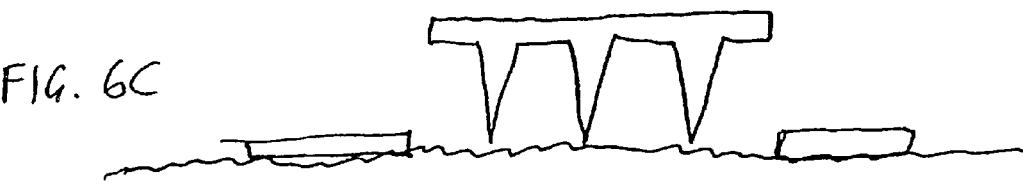
FIGS. 6C-6E illustrate schematically a sequence of penetration of microneedles through the skin employing a variable-geometry skin stretching technique according to the teachings of the present invention.
Figure 6D:
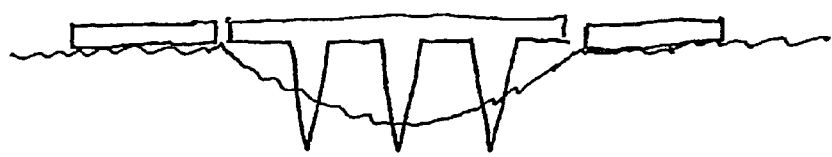
Figure 6E:
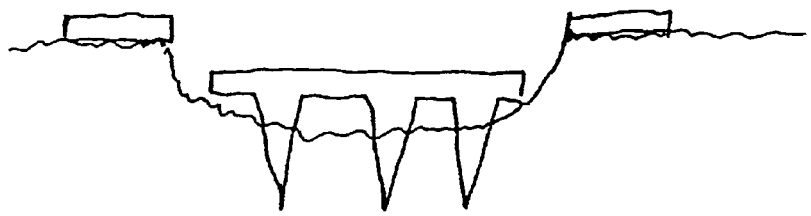

Turning now to FIGS. 6C-6E, these illustrate a second penetration enhancement technique in which one or more abutment surfaces are made to temporarily adhere to a surface of the biological barrier. The fluid transport configuration is then displaced relative to the abutment surfaces along a path of movement which carries the substantially planar microneedle-supporting surface from an initial position above the abutment surfaces (FIG. 6C) to a deployed position projecting below the abutment surfaces (FIG. 6E) so as to stretch the biological barrier across the substantially planar surface.

Referring now again to FIGS. 1-5B, device 10 is preferably provided with a displacement mechanism mechanically linking between base 14 and fluid transport unit 12 which defines a path of movement so as to achieve both the directional insertion and the variable-geometry skin stretching features simultaneously. Specifically, this requires a displacement mechanism which defined a path of movement such that:

at least part of the path of movement has a non-zero component parallel to the microneedle support surface 16; and the path carries microneedle support surface 16 from an initial position above abutment surfaces defined by base 14 to a deployed position projecting below the abutment surfaces.

Parenthetically, it should be noted that the terms "above" and "below" are used herein arbitrarily to denote the up and down directions, respectively, as viewed in the orientation of FIGS. 1-5B. In other words, "up" or "above" indicates a direction or position away from the biological barrier while "down" or "below" denotes a direction or position towards the biological barrier. It is important to note however that, notwithstanding this terminology, preferred implementations of the present invention may in fact be used equally in any required orientation.

In the implementation shown, the displacement mechanism includes profiled slots 20 formed in base 14 within which corresponding pins 22 of fluid transport unit 12 slide. The lateral component of the movement may be a short motion occurring at any stage after contact between the microneedles and the skin in a movement which is generally downward, perpendicular to the skin. Alternatively, the substantially the entire motion may be an inclined sliding motion which has a lateral component to the motion vector throughout. The paired slots 20 on either side of the base 14 ensure that fluid transport unit 12 undergoes parallel movement, i.e., without tilting relative to the base. The sequence of positions of fluid transport unit 12 relative to the base 14 is best illustrated in FIGS. 2A-4B. Preferably, the fluid delivery unit locks into its final deployed position to ensure structural stability of the device. The locking effect may be provided simply by the angle of the end portion of slots 20, or may be the result of a positive locking element (not shown) which obstructs return of pins 22. Preferably, subsequent removal of the device is performed by first reversing the direction of movement of the fluid transport unit so that the needles go back along the same entry paths, thereby minimizing trauma to the skin.

It will be appreciated that the pin and slot configuration illustrated here is just one of a large number of possible displacement mechanisms which can be used to define or generate the required motion. Other preferred examples (not illustrated) include, but are not limited to, a reversed arrangement of slots in unit 12 and pins from the base 14; an arrangement of lever arms; and an arrangement of spring elements.

In order to maximize effectiveness of the directional insertion technique of the present invention, device 10 preferably uses microneedle structures with one or more distinctive properties as follows.

According to a first preferred feature, each microneedle 18 is asymmetrical such that a "base-to-tip vector" is non-perpendicular to microneedle supporting surface 16. The directionality of the "base-to-tip vector" is then coordinated with the insertion path so as to enhance the penetration effect of the lateral (in-plane) displacement component as illustrated conceptually in FIG. 6B.

The calculation of the "base-to-tip vector" for various microneedle structures is illustrated graphically in FIGS. 7A-9B. Geometrically, the "base-to-tip vector" is typically defined as a vector from a centroid of a base area of the microneedle to a centroid of a penetrating tip of the microneedle. In this context, the "centroid" of a shape is a point in the plane of a two-dimensional shape which, when used as an origin, the vector sum over the area of the shape is zero. In other words, the centroid corresponds to the center of mass of a thin slice of uniform weight per unit area corresponding to the shape of the cross-section. In the case of the microneedles of the present invention, the base centroid is the centroid of a cross-section of the microneedle form taken in the plane of surface 16. Similarly, the tip centroid is the centroid of the area of a cross-section taken through the microneedle tip parallel to surface 16. In the case of a pointed microneedle, the tip centroid is effectively the sharp point itself.

Figure 7A:
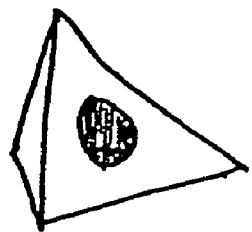
FIG. 7A is a schematic isometric view of a microneedle structure according to a first preferred implementation of the present invention.
Figure 7B:
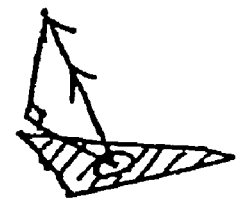
FIG. 7B is a geometrical representation of a base-to-tip vector for the microneedle of FIG. 7A.

As illustrated in FIGS. 7A-9B, it should be noted that a wide range of microneedle structures satisfy the above-mentioned asymmetry requirement. In the case of FIGS. 7A and 7B, there is shown a particularly preferred triangular-profile microneedle structure of a type disclosed in the aforementioned PCT publication no. WO 02/17985, incorporated herein by reference. In this case, the base is substantially triangular such that the centroid falls somewhere near the intuitive "center" of the triangle. The penetrating point, on the other hand, is formed at the intersection of an inclined face with at least one substantially upright wall. As a result, the tip centroid is defined by the penetrating point which is located roughly above one of the corners of the triangular base. The resulting base-to-tip vector is illustrated in FIG. 7B and has a significant in-plane component.

Parenthetically, it should be noted that the microneedle form of FIG. 7A is believed to be particularly advantageous for the mechanical support it provides to both the tip and the upright walls which make is highly suited to withstand the directional insertion without breakage. Furthermore, fluid transfer is greatly enhanced by use of a microneedle structure where a fluid transfer conduit intersects the microneedle surfaces at a position proximal to a solid penetrating tip, such as in this structure, thereby avoiding plugging of the conduit. A still further advantage of this form will be discussed below with reference to FIGS. 10A and 10B.

Figure 8A:
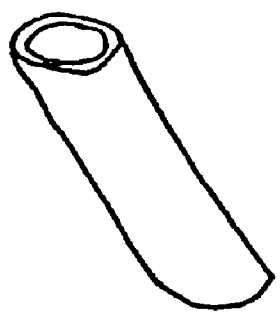
FIGS. 8A and 8B are a schematic isometric view of a first alternative microneedle structure and the corresponding base-to-tip vector geometry, respectively.
Figure 8B:
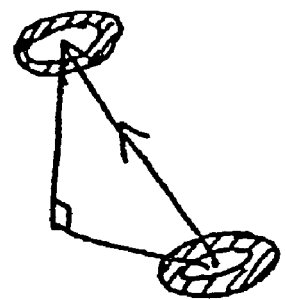

Turning now to FIGS. 8A and 8B, these show an alternative asymmetric hollow microneedle design as a tilted cylinder. In this case, the base and tip shapes are generally similar, but an in-plane component of the base-to-tip vector results from the "tilt" of the needle.

Figure 9A:
FIGS. 9A and 9B are a schematic isometric view of a second alternative microneedle structure and the corresponding base-to-tip vector geometry, respectively.
Figure 9B:

Turning now to FIGS. 9A and 9B, these show a further alternative microneedle design in which the major part of the microneedle is a symmetrical straight-standing hollow cylinder. In this case, the "asymmetry" is provided by a beveled tip portion which results in the centroid of the tip being on the periphery of the cylinder. Since the centroid of the base is on the axis of the cylinder, this form also satisfies the aforementioned definition of a base-to-tip vector with a component parallel to the base surface.

It should be noted that, in general, it is considered preferable that the centroid of a cross-section of the microneedle at half its height is also displaced parallel to the base surface relative to the base centroid. This additional condition requires asymmetry of the body of the microneedle rather than just its tip, thereby excluding the case of FIG. 9A. Most preferably, the microneedle also exhibits a monotonically decreasing cross-sectional area with increasing height (i.e. distance from the base surface) such as is exhibited by the form of FIG. 7A. Another preferred feature is that a projection of the penetrating tip onto the planar surface lies within the base area of the microneedle. This condition is also satisfied by the form of FIG. 7A with vertical or slightly inwardly sloped upright walls, and contributes greatly to the mechanical integrity of the structure.

Referring now to FIGS. 10A-11B, there is illustrated a further alternative, or additional, preferred feature of the microneedle structure for directional insertion through a biological barrier. According to this feature, each microneedle is formed with at least two side walls which form a relatively sharp edge between them. Geometrically, a substantially planar face of each side wall is positioned such that an angle θ between the faces as measured in a plane parallel to the microneedle-supporting base surface is no greater than 90°, and preferably between 30° and 70°. It should be noted that the angle mentioned is defined between the substantially planar portions of the faces and does not exclude the possibility of rounding of the edge between the faces. This feature is effective in facilitating cutting of the biological barrier during directional insertion, even where the edge between the faces is somewhat rounded.

Figure 10A:
FIG. 10A is a schematic isometric view of a microneedle similar to that of FIG. 7A illustrating an insertion direction.
Figure 10B:
FIG. 10B is a plan view of the microneedle of FIG. 10A illustrating an angular relation of two side walls to form a cutting edge formation.
Figure 11A:
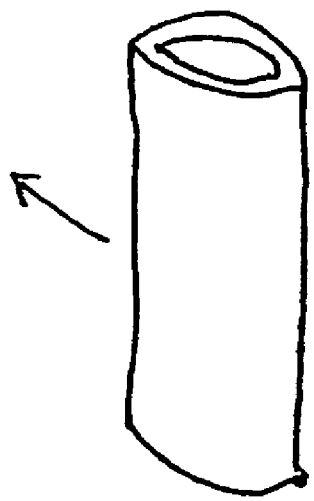
FIG. 11A is a schematic isometric view of a further alternative microneedle structure for use in the present invention.
Figure 11B:
FIG. 11B is a plan view of the microneedle of FIG. 1A illustrating an angular relation of two side walls to form a cutting edge formation.

Turning now specifically to FIGS. 10A and 10B, these illustrate again the preferred triangular-profile microneedle structure which exhibits the cutting-edge feature as defined. FIGS. 11A and 11B illustrate an alternative microneedle structure which exhibits this cutting-edge feature. In this case, a symmetrical upright microneedle is formed with two curved walls which meet at an angle θ on both sides of the central channel.

In all cases where this cutting-edge property is used, the direction of insertion is clearly chosen to have a component in the direction in which the cutting edge "points", and specifically, such that the in-plane component of the insertion direction for at least part of the path of motion lies within the range of angles θ as illustrated in the plan views of FIGS. 10B and 11B.

Referring now again to the skin-stretching aspect of the present invention, as described earlier, this operates by first adhering one or more abutment surface to the biological barrier while the barrier is substantially flat, and then generating relative motion between the fluid transfer unit and the abutment surface(s) so as to effectively stretch the biological barrier across the substantially planar surface, thereby enhancing microneedle penetration. Adhesion can be achieved by the use of a wide range of adhesives or adhesive tapes which are designed for use in medical applications, as are well known in the art.

Most preferably, the at least one abutment surface substantially encircles the fluid transport configuration when the planar surface is in the deployed position. This ensures stretching of the biological barrier across the microneedle region in two directions. In the implementation of FIGS. 1-5B, the abutment surface is provided by a continuous lower surface 24 of base 14 which serves as a roughly rectangular frame around the contact region of the microneedles.

Figure 12:
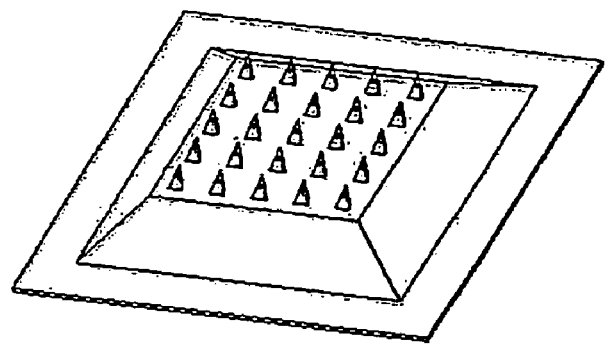
FIG. 12 is an enlarged isometric view of a preferred configuration for a microneedle array for use in the device of FIG. 1.

In order to enhance the effectiveness of this stretching technique, the microneedles 18 may advantageously be positioned on a localized plateau immediately surrounded by rearward-sloping or rearward-curving surfaces (referred to as "ramps"). The distance between the peripheral microneedles and the beginning of the ramp is preferably less than the lateral dimension of the microneedle region, and is most preferably no more than about 1 mm. An example of such a structure is illustrated in FIG. 12.

Finally with regard to penetration enhancement, a further preferred feature for enhancing penetration of the microneedles is the use of mechanical vibrations, preferably in the ultrasonic frequency range. This feature is also believed to be useful and patentable independently of the other features of the present invention, but is preferably used in synergy with some or all of the other features. In the example of FIGS. 1-5B, this is illustrated as an ultrasonic drive unit 26 associated with fluid transfer unit 12. Various implementations of an ultrasonic drive unit, typically an electronically driven piezoelectric actuator, are known.

Ultrasonic drive unit is of additional importance for various therapeutic effects. In addition to its mechanical penetration enhancement effect, the ultrasonic vibrations enhance the distribution of a drug delivered to the body tissue. In the case of immunizations and the like where genetic or other material must be injected into cells, the vibrations are particularly effective for enhancing penetration of biological material into the cells.

Turning now to the features of fluid transfer unit 12 in more detail, as mentioned earlier, according to one particularly preferred set of embodiments, fluid transfer unit 12 is implemented as a fluid transfer arrangement for generating a high-speed liquid jet for supplementing mechanical penetration of the microneedles by jet injection. The implementation illustrated here is best seen in the cross-sectional views of FIGS. 4B and 5B before and after actuation, respectively. Although illustrated in the context of device 10, it will be appreciated that the combination microneedle and jet-injection aspect of the present invention may alternatively be implemented independently from the aforementioned penetration enhancing features.

Generally speaking, the fluid transfer arrangement includes a cylinder 30 which houses a quantity of a liquid composition to be injected in a storage region 30a. Storage region 30a is in fluid connection with the microneedle interface (substrate and array of hollow microneedles as described above). A hand-operated cover 32 is manually depressible so as to apply force to a piston 34 which forces the liquid through the hollow microneedles to form fine jets therefrom.

It is a preferred feature of the present invention that the device is configured to prevent initial flow of the liquid through the microneedles until the applied manual pressure is sufficient to ensure a resultant fluid pressure, at least momentarily, of at least about 1000 pounds per square inch (psi). Most preferably, this is achieved by placing an appropriately designed breakable membrane or "diaphragm" 36 between the initial location of the liquid and the microneedles. The diaphragm is designed, typically with lines of reduced thickness or strength, to fracture within a predefined range of applied pressure. The range is typically chosen to be between about 1000 and about 1500 PSI. This structure also ensures that the liquid cannot escape prematurely from the microneedles and is sealed from the atmosphere prior to use.

The liquid may be either loaded directly into the cylinder as shown or located in a capsule or cartridge (not shown). In either case, a priming or mixing action may be performed shortly prior to, or during, the initial application of pressure to the piston.

In order to prevent unintentional operation of the fluid transfer arrangement, and to ensure sufficient applied force to generate the required jets, a mechanical obstruction is preferably provided. In the embodiment illustrated here, the obstruction is implemented as a disk 38 associated with piston 34 which is obstructed by inward projections 40. Projections 40 are configured to break off when a required threshold force (e.g. 1 kg force) is applied to cover 32. Alternatively, a resiliently deformable obstacle may be used to perform the same function.

As in the prior PCT publications incorporated by reference above, the definition of the term "microneedle" in this context is taken to be a needle of length (or "height" as viewed standing from the surface of a substrate) of less than 2 mm. The actual height used is chosen in coordination with the designed jet injection penetration depth according to the desired application, as will be detailed below. In each case, the microneedles themselves must be sufficiently large to ensure penetration of the stratum corneum layer. In most cases, a minimum height is about 50 microns. This ensures that the tough outer layers of the skin are penetrated mechanically prior to actuation of the liquid jet. Maximum height is preferably kept below about 1 mm, and more preferably up to about 0.6 mm, so as to minimize discomfort.

The jet injection effect is designed to penetrate at least an additional 50% of the microneedle height, giving a total penetration depth of at least one-and-a-half time, and more preferably 2-3 times, the mechanical microneedle penetration depth. For shallow intra-cutaneous delivery within the epidermis, total delivery depths in the range from about 20 microns to 100 or 200 microns are required. For intra-dermal delivery a total depth of between 0.2 and 2 mm is required. For sub-cutaneous delivery, total depths over 2 mm are required.

The bore of the hollow microneedles, and the resulting output liquid jet, preferably has a diameter of between about 0.03 mm-0.07 mm. Other dimensions and spacing of the microneedles are preferably as described in the aforementioned PCT publications, although other values may be used according to the requirements of a given application.

The preferred diameter of the piston-cylinder configuration generating the jet pressure is no more than about 2 mm, and preferably between 1 and 2 mm. It will be appreciated that manual application of about 1 or 2 kg force to this area generates between about 70 and about 300 kg per square cm (about 1000 to about 4000 psi). Typically, lower pressure is required for a given depth of penetration compared to conventional jet injection techniques due to the initial penetration of the hard outer skin layers by the microneedles.

As a result of the channel formed by penetration of the liquid jet into the epidermal, dermal and/or sub-dermal tissue and the high speed delivery pulse, the total delivery time is typically less than a second for a delivered volume of between about 0.1 and about 2 micro-liters (cubic millimeters) per jet. The number of microneedles in the array may be chosen appropriately (typically between about 25 and about 1000) to provide a required total delivery volume distributed over the area of the microneedle array. The device is thus particularly suitable for delivering liquid quantities in the range 1-1000 micro-liters.

Turning briefly to the breakable membrane or diaphragm 36, this is based on a concept commonly used in many mechanical systems such as safety devices in various high pressure systems. The diaphragm may be implemented as a sphere with accurate thickness; a layer or film with accurate thickness; or as a layer or film with accurate thickness and in addition weakened at the center by making mark or pattern. The option of a predefined breaking pattern may have advantages for ensuring that the remnants do not form any blockage of flow through the device.

The operation of the device of the present invention and the corresponding broad method will now be clearly understood. The method in its broadest sense may be regarded simply as the steps of: (a) penetrating outer layers of skin to a depth of less than 2 mm, and preferably less than 0.6 mm, with at least one hollow microneedle; and (b) generating a flow of liquid through the bore(s) of the microneedle(s) with sufficient speed to achieve jet injection through tissue beyond the depth of penetration of the microneedle(s). The energy for the flow is preferably provided exclusively by manually applied force. The preferred parameters of the device used to implement the method are the preferred parameters of the device as described above.

Figure 13A:
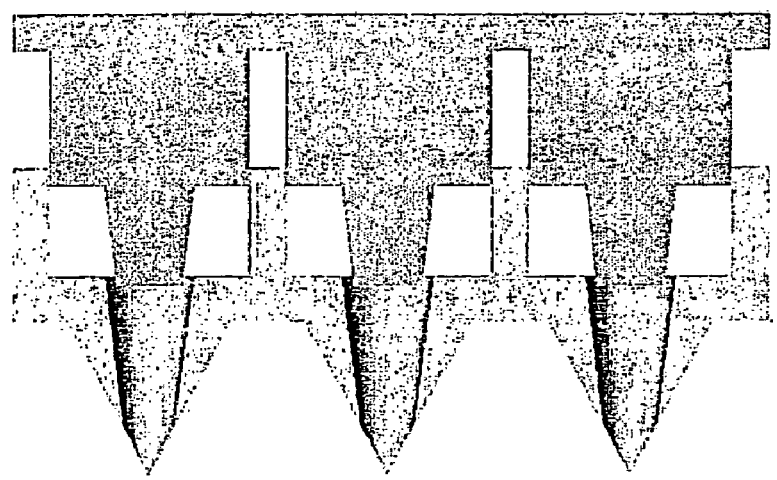
FIG. 13A is a schematic cross-sectional view through an alternative implementation of a microneedle array configuration for the device of FIG. 1 prior to actuation.
Figure 13B:
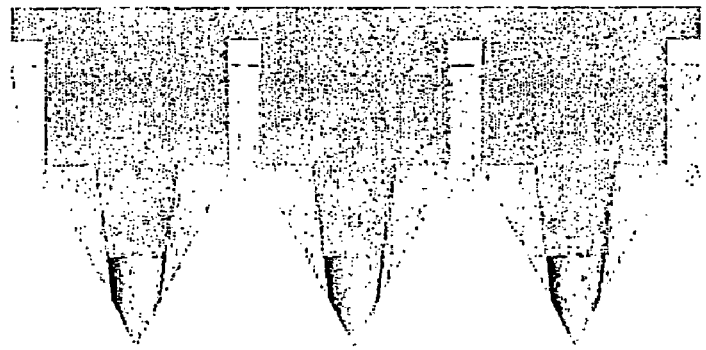
FIG. 13B is a view similar to FIG. 13A showing the microneedle array configuration after actuation.

Turning now to FIGS. 13A and 13B, there is shown schematically an alternative microneedle jet injection configuration for use in the present invention. In this case, the bore of each microneedle is formed as a hollow conical bore and the piston is formed with a corresponding number of complementary solid truncated conical projections. As the projections enter the microneedle bores, they form a narrow converging conical flow pattern which is highly effective for generating a high-speed liquid jet.

Figure 14:
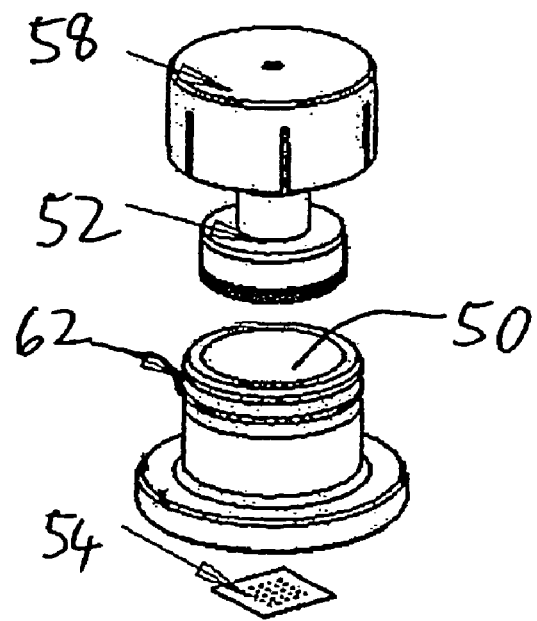
FIG. 14 is a schematic isometric exploded view of an alternative fluid delivery device for use in the device of FIG. 1.
Figure 15:
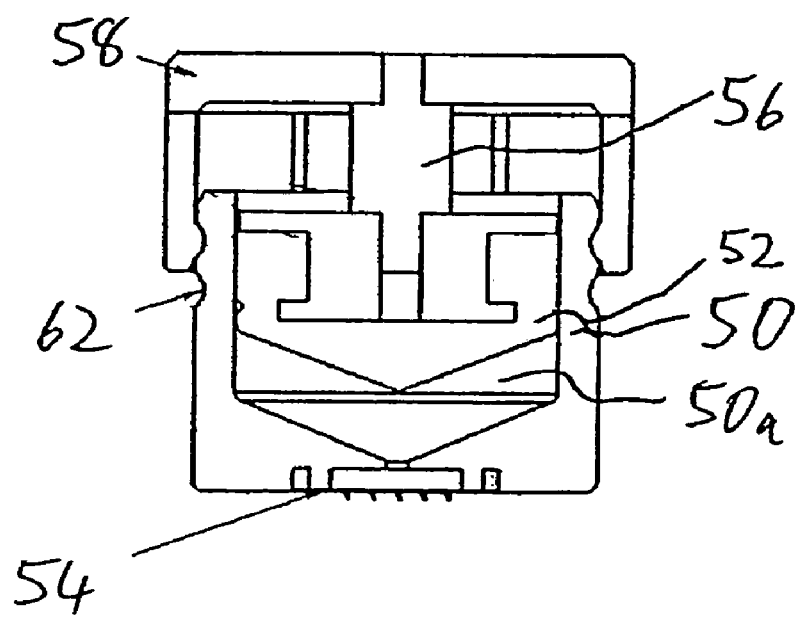
FIG. 15 is a cross-sectional view taken through the fluid delivery device of FIG. 14 when assembled.

Finally, turning to FIGS. 14 and 15, although described herein in a preferred implementation using a jet injection configuration, it should be appreciated that the penetration enhancement features of the present invention may alternatively be implemented with slow flow-rate delivery devices, with diagnostic sampling devices, and with any other microneedle-based device where effective penetration is required. By way of one additional preferred example, FIGS. 14 and 15 illustrate a fluid transfer configuration for relatively large volume slow drug delivery.

Generally speaking, the fluid transfer configuration of FIGS. 14 and 15 is similar to that of FIGS. 1-5B, with a cylinder 50 defining a liquid storage volume 50a and a piston 52 for driving the liquid to the microneedle interface 54. In this case, the piston is a large area piston which typically needs to apply driving pressure to the liquid over a period of at least a minute, and possible for significantly longer periods. A spring element is preferably used to maintain the driving pressure.

In the case illustrated here, an elastomeric spring element 56 is compressed by forcing a cover 58 from its initial position as shown in FIG. 15 to a lowered position where resilient tabs 60 engage in lower lateral recessed 62. Once the cover is depressed, the compressed spring element maintains continuous pressure in the liquid during a period of operation. Clearly, elastomeric spring element 56 may be replaced by other types and arrangements of springs, or by a suitably designed flexible cap which itself stores sufficient elastic deformation to provide the continuous pressure required to drive the fluid flow.

Here too, the fluid transfer configuration is preferably mounted relative to the base 14 (FIG. 1) via any suitable displacement mechanism (not shown) such as a system of pins or lever arms, as will be clear to one ordinarily skilled in the art.

It will be appreciated that the above descriptions are intended only to serve as examples, and that many other embodiments are possible within the scope of the present invention as defined by the appended claims.

What is claimed is:

1. A microneedle device for transporting fluid across a biological barrier, the device comprising:
   (a) a fluid transport configuration including:
      (i) a substrate defining a substantially planar surface,
      (ii) a plurality of microneedles projecting from said substantially planar surface, and
      (iii) for each of said microneedles, a conduit extending through at least part of said microneedle, said conduit being configured to provide a fluid flow path for transport of fluids;
   (b) an abutment member having at least one abutment surface for abutting the biological barrier, said abutment member configured to anchor a region of the biological barrier so as to oppose movement of the biological barrier parallel to a surface of the biological barrier; and (c) a displacement mechanism mechanically linking between said abutment member and said fluid transport configuration, said displacement mechanism defining a path of movement of said fluid transport configuration relative to said abutment surface, at least part of said path of movement being such that, when said abutment member is anchored to the biological barrier and said displacement mechanism is actuated, said microneedles move relative to an initial position of the biological barrier together, while in contact with the biological barrier, in a direction having a non-zero component parallel to the surface of the biological barrier.

2. The device of claim 1, wherein each of said microneedles has a base-to-tip vector defined as a vector from a centroid of a base area of said microneedle to a centroid of a penetrating tip of said microneedle, said microneedles being asymmetrical such that said base-to-tip vector is non-perpendicular to said substantially planar surface, a direction parallel to a projection of said base-to-tip vector on to said substantially planar surface being taken to define a penetration direction, and wherein at least part of said path of movement has a non-zero component along said penetration direction.

3. The device of claim 2, wherein each of said microneedles is formed such that a projection of said penetrating tip onto said substantially planar surface lies within said base area of said microneedle.

4. The device of claim 1, wherein each of said microneedles is formed with at least one upright surface standing substantially perpendicular to said substantially planar surface and at least one inclined surface inclined relative to a perpendicular to said substantially planar surface, said conduit intersecting said inclined surface.

5. The device of claim 1, wherein each of said microneedles is formed with at least two substantially planar surfaces, said surfaces being positioned such that an angle between said surfaces as measured in a plane parallel to said substantially planar surface of said base is no greater than 90°.

6. The device of claim 5, wherein said angle between said surfaces is between 30° and 70°.

7. The device of claim 1, wherein said conduit intersects a surface of said microneedle proximal to said penetrating tip.

8. The device of claim 1, further comprising a flow actuation mechanism in fluid connection with said conduits and configured for generating a driving pressure of at least 1000 PSI so as to produce a high velocity fluid jet emerging from said conduits for penetrating into the biological barrier beyond a depth of penetration of said microneedles.

9. The device of claim 1, wherein at least part of said at least one abutment surface is provided with adhesive for maintaining contact between said abutment surface and the biological barrier.

10. The device of claim 9, wherein said path of movement carries said substantially planar surface from an initial position above said at least one abutment surface to a deployed position projecting below said at least one abutment surface for stretching the biological barrier across said substantially planar surface.

11. The device of claim 1, further comprising a vibration generator associated with said fluid transport configuration and deployed so as to generate vibration of said fluid transport configuration so as to enhance penetration of said microneedles into the biological barrier.

12. A method for transporting fluid across a biological barrier comprising the steps of:
(a) providing a fluid transport configuration including:
(i) a substrate defining a substantially planar surface,
(ii) a plurality of microneedles projecting from said substantially planar surface, and
(iii) for each of said microneedles, a conduit extending through at least part of said microneedle, said conduit being configured to provide a fluid flow path for transport of fluids;
(b) positioning said fluid transport configuration in contact with the biological barrier; and
(c) displacing said fluid transport configuration so that said microneedles move together in contact with said biological barrier along a common path of movement relative to an initial position of the biological barrier, said path having a non-zero component parallel to said substantially planar surface,
wherein each of said microneedles has a base-to-tip vector defined as a vector from a centroid of a base area of said microneedle to a centroid of a penetrating tip of said microneedle, said microneedles being asymmetrical such that said base-to-tip vector is non-perpendicular to said substantially planar surface, a direction parallel to a projection of said base-to-tip vector on to said substantially planar surface being taken to define a penetration direction.

13. The method of claim 12, wherein each of said microneedles is formed such that a projection of said penetrating tip onto said substantially planar surface lies within said base area of said microneedle.

14. The method of claim 12, wherein each of said microneedles is formed with at least one upright surface substantially perpendicular to said substantially planar surface and at least one inclined surface inclined relative to a perpendicular to said substantially planar surface, said conduit intersecting said inclined surface.

15. The method of claim 12, wherein each of said microneedles is formed with at least two substantially planar surfaces, said at least two surfaces being positioned such that an angle between said surfaces as measured in a plane parallel to said substantially planar surface of said base is no greater than 90°.

16. The method of claim 15, wherein said angle between said surfaces is between 30° and 70°.

17. The method of claim 12, wherein said conduit intersects a surface of said microneedle proximal to said penetrating tip.

18. The method of claim 12, further comprising generating a high velocity flow of fluid through a bore of the microneedle so as to form a fluid jet with sufficient pressure to penetrate into the biological barrier to a total depth at least one-and-a-half times a penetration depth of said microneedles.

19. The method of claim 12, further comprising positioning at least one abutment surface in contact with said biological barrier, said displacing of said fluid transport configuration being performed relative to said abutment surface.

20. The method of claim 19, wherein said at least one abutment surface is made to adhere temporarily to said biological barrier.

21. The method of claim 20, wherein said displacing of said fluid transport configuration carries said substantially planar surface from an initial position above said at least one abutment surface to a deployed position projecting below said at least one abutment surface so as to stretch the biological barrier across said substantially planar surface.

22. The method of claim 12, further comprising inducing vibration of said fluid transport configuration so as to enhance penetration of the microneedles into the biological barrier.

23. The method of claim 12, wherein said path of movement is substantially parallel to said penetration direction.

24. The method of claim 12, wherein said path of movement has a positive component along said penetration direction.

25. A method for transporting fluid across a biological barrier comprising the steps of:
(a) providing a fluid transport configuration including:
   (i) a substrate defining a substantially planar surface,
   (ii) a plurality of microneedles projecting from said substantially planar surface, and
   (iii) for each of said microneedles, a conduit extending through at least part of said microneedles, said conduit being configured to provide a fluid flow path for transport of fluids;
(b) positioning said fluid transport configuration in contact with the biological barrier; and
(c) displacing said fluid transport configuration so that said microneedles move together in contact with said biological barrier along a common path of movement relative to an initial position of the biological barrier, said path having a non-zero component parallel to said substantially planar surface,
wherein each of said microneedles is formed with at least one side wall standing substantially perpendicular to said substantially planar surface and at least one wall inclined relative to a perpendicular to said substantially planar surface.

26. A method for transporting fluid across a biological barrier comprising the steps of:
(a) providing a fluid transport configuration including:
   (i) a substrate defining a substantially planar surface,
   (ii) a plurality of microneedles projecting from said substantially planar surface, and
   (iii) for each of said microneedles, a conduit extending through at least part of said microneedle, said conduit being configured to provide a fluid flow path for transport of fluids;
(b) positioning said fluid transport configuration in contact with the biological barrier; and
(c) displacing said fluid transport configuration so that said microneedles move together in contact with said biological barrier along a common path of movement relative to an initial position of the biological barrier, said path having a non-zero component parallel to said substantially planar surface,
wherein each of said microneedles is formed with at least two side walls each having a substantially planar face, said side walls being positioned such that an angle between said faces as measured in a plane parallel to said substantially planar surface of said base is no greater than 90°.

27. The method of claim 26, wherein said angle between said faces is between 30° and 70°.

* * * * *